(12) United States Patent
Greer et al.

(10) Patent No.: US 11,000,644 B2
(45) Date of Patent: May 11, 2021

(54) EQUIPMENT CADDY FOR DEMOUNTABLE ENGAGEMENT WITH A SINGLE-POLE ROLLING STAND

(71) Applicant: Ridgeline Medical Supply Inc., Bragg Creek (CA)

(72) Inventors: Stephen Greer, Bragg Creek (CA); Scott Berry, Bragg Creek (CA)

(73) Assignee: Ridgeline Medical Supply Inc., Bragg Creek (CA)

( * ) Notice: Subject to any disclaimer, the term of this patent is extended or adjusted under 35 U.S.C. 154(b) by 0 days.

(21) Appl. No.: 15/833,776

(22) Filed: Dec. 6, 2017

(65) Prior Publication Data

US 2019/0143030 A1    May 16, 2019

Related U.S. Application Data

(60) Provisional application No. 62/586,357, filed on Nov. 15, 2017.

(51) Int. Cl.
  *A61M 5/14* (2006.01)
  *F16M 11/00* (2006.01)
  *A61G 5/10* (2006.01)
  *A61G 12/00* (2006.01)

(52) U.S. Cl.
  CPC ......... *A61M 5/1415* (2013.01); *A61G 12/008* (2013.01); *A61M 2209/084* (2013.01)

(58) Field of Classification Search
  CPC .......... A61M 2209/084; A61M 5/1415; A61M 5/1417; A61G 7/0503; A61G 12/008; A61G 2203/80; A61G 12/002; A61G 12/004; A61H 2003/002; A61H 2003/004

USPC ............... 482/68, 142; 211/107; 220/475; 248/124, 145.6, 312, 229, 129
See application file for complete search history.

(56) References Cited

U.S. PATENT DOCUMENTS

| | | | | |
|---|---|---|---|---|
| 3,552,577 A | * | 1/1971 | Latham, Jr. ........ | A61B 10/0096 211/74 |
| 4,266,765 A | * | 5/1981 | Sandoval ............... | A61G 12/00 280/47.371 |
| 4,832,294 A | * | 5/1989 | Eidem ................. | A61M 5/1415 248/125.8 |

(Continued)

OTHER PUBLICATIONS

Merriam Webster Dictionary "Housing" https://www.merriam-webster.com/dictionary/housing Accessed Aug. 17, 2020 (Year: 2020).*

*Primary Examiner* — Gideon R Weinerth
(74) *Attorney, Agent, or Firm* — Gowling WLG (Canada) LLP

(57) ABSTRACT

Disclosed herein is an equipment caddy for demountable engagement with a rolling stand. The caddy comprises a hub defining an opening for receiving a vertically oriented pole of the stand and a housing defining a compartment that is distal to the hub and configured to demountably engage with a piece of equipment. One embodiment relates to a medical equipment caddy for demountable engagement with a rolling IV stand wherein the housing is configured to demountably engage with a piece of medical equipment. The caddy of the present disclosure is durable, easy to clean and disinfect, and inexpensive to produce. The caddy of the present disclosure provides means for transporting additional medical equipment upon a conventional IV stand in a simple and organized manner.

3 Claims, 4 Drawing Sheets

(56) References Cited

U.S. PATENT DOCUMENTS

| | | | |
|---|---|---|---|
| D310,570 S * | 9/1990 | Wells | D24/128 |
| 5,114,023 A * | 5/1992 | Lavin | A47B 57/54 |
| | | | 211/107 |
| 5,149,036 A * | 9/1992 | Sheehan | A61G 7/0503 |
| | | | 248/215 |
| D345,017 S * | 3/1994 | Fischer | D24/128 |
| 5,337,992 A * | 8/1994 | Pryor | A61G 7/0503 |
| | | | 248/125.1 |
| 5,479,953 A * | 1/1996 | Pasulka | A61H 3/04 |
| | | | 135/66 |
| D391,636 S * | 3/1998 | Zwerk | D24/128 |
| 5,890,687 A * | 4/1999 | Pryor | A61M 5/1415 |
| | | | 248/125.8 |
| 6,390,311 B1 * | 5/2002 | Belokin | A61M 5/1415 |
| | | | 211/189 |
| 6,405,882 B1 * | 6/2002 | Baxter | B63C 11/18 |
| | | | 211/74 |
| 6,708,991 B1 * | 3/2004 | Ortlieb | A61M 5/1415 |
| | | | 248/122.1 |
| 7,490,837 B2 * | 2/2009 | Pond | A61B 17/00 |
| | | | 280/47.35 |
| 7,731,136 B1 * | 6/2010 | Chisolm | A61M 5/1415 |
| | | | 211/204 |
| D627,063 S * | 11/2010 | West | D24/128 |
| 7,935,030 B1 * | 5/2011 | Nesbitt | A61H 3/04 |
| | | | 482/142 |
| 7,959,122 B1 * | 6/2011 | Clack-Hopkins | A61M 5/1417 |
| | | | 248/316.7 |
| 8,152,181 B2 * | 4/2012 | Tomlinson | A61M 5/1417 |
| | | | 280/47.34 |
| 8,292,310 B2 * | 10/2012 | Turner | A61H 3/04 |
| | | | 280/47.35 |
| D692,132 S * | 10/2013 | Damron | D24/128 |
| 9,033,349 B2 * | 5/2015 | Graves | A47C 7/62 |
| | | | 280/47.35 |
| D733,891 S * | 7/2015 | Murray | D24/185 |
| 9,121,423 B2 * | 9/2015 | Sharpe | F16M 11/105 |
| 9,883,978 B2 * | 2/2018 | Blankenship | A61M 5/1414 |
| 10,151,425 B1 * | 12/2018 | Bileth | B25H 3/06 |
| 2002/0096608 A1 * | 7/2002 | Cedarberg, III | A61M 5/1418 |
| | | | 248/125.3 |
| 2004/0207244 A1 * | 10/2004 | McKellar | A61G 5/1094 |
| | | | 297/463.1 |
| 2007/0267551 A1 * | 11/2007 | Townsend | A61M 5/1415 |
| | | | 248/125.8 |
| 2008/0012257 A1 * | 1/2008 | Gregg | B62B 3/12 |
| | | | 280/47.35 |
| 2008/0263769 A1 * | 10/2008 | Newkirk | A61G 7/05 |
| | | | 5/503.1 |
| 2008/0272571 A1 * | 11/2008 | Turner | A61H 3/04 |
| | | | 280/202 |
| 2009/0085317 A1 * | 4/2009 | Livengood | A61H 3/04 |
| | | | 280/79.3 |
| 2009/0294604 A1 * | 12/2009 | Sunderland | A61M 5/1415 |
| | | | 248/124.1 |
| 2009/0294622 A1 * | 12/2009 | Medders | A47B 81/04 |
| | | | 248/523 |
| 2010/0052274 A1 * | 3/2010 | West | A61M 5/1417 |
| | | | 280/47.24 |
| 2011/0278809 A1 * | 11/2011 | Turner | A61H 3/04 |
| | | | 280/47.35 |
| 2013/0228997 A1 * | 9/2013 | Fukuhara | A61M 5/1417 |
| | | | 280/304.1 |
| 2015/0182690 A1 * | 7/2015 | Rowston | A61M 5/1413 |
| | | | 211/85.13 |
| 2016/0114102 A1 * | 4/2016 | Yamamoto | A61M 5/1415 |
| | | | 108/27 |
| 2017/0363247 A1 * | 12/2017 | Koehler | A61M 5/1417 |
| 2018/0207353 A1 * | 7/2018 | Hesketh | A61M 5/1417 |

\* cited by examiner

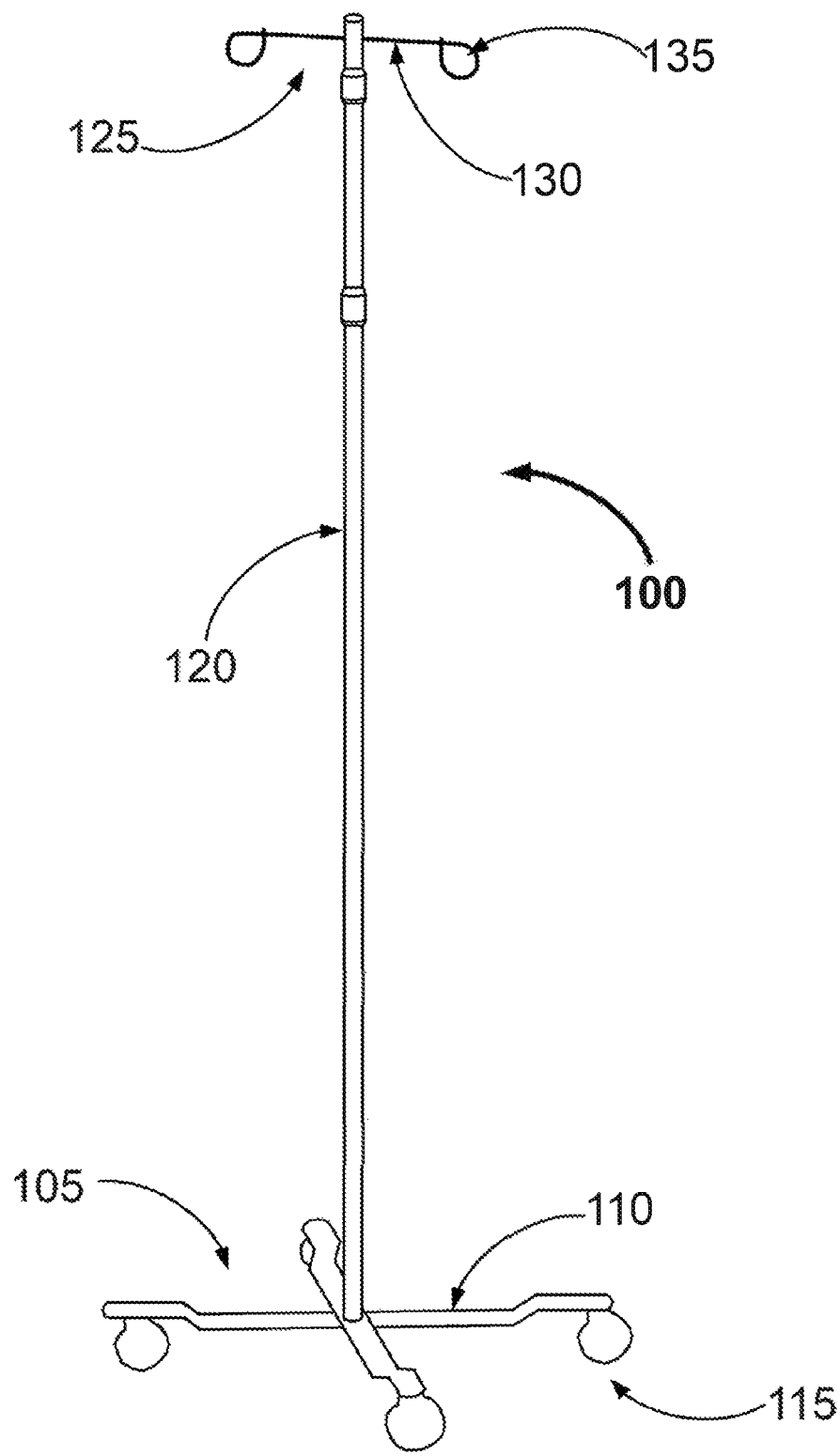
FIG. 1 (*Prior Art*)

EQUIPMENT CADDY FOR DEMOUNTABLE ENGAGEMENT WITH A SINGLE-POLE ROLLING STAND

CROSS-REFERENCE TO RELATED APPLICATIONS

This application is a U.S. Nonprovisional Application filed under 35 U.S.C. § 111(a) which claims the benefit of U.S. Application No. 62/586,357, filed Nov. 15, 2017. This application is hereby incorporated by reference in its entirety.

TECHNICAL FIELD

The present disclosure generally relates to equipment caddies for transport on single-pole rolling stands. In particular, the present disclosure relates to medical equipment caddies for demountable engagement with rolling IV stands.

BACKGROUND

Intravenous stands, also referred to as IV stands or IV poles, are used in a variety of therapeutic and/or diagnostic settings to enable patients to ambulate while connected to IV bags. Conventional IV stands include a base assembly configured to roll on the floor, a support pole which extends vertically from the base assembly, and a hanger assembly approximate the top of the support pole. At least one bag containing an IV solution may be suspended from the hanger assembly.

While conventional IV stands are generally sufficient for ambulatory patients connected only to IV-related medical equipment, they do not adequately address the needs of ambulatory IV patients requiring additional medical equipment. As such, IV patients requiring additional medical equipment (and their healthcare professionals) are left to improvise means for transporting additional medical equipment alongside conventional IV stands. This is problematic in that it consumes time which may otherwise be invested in patient recovery and care. Moreover, improvised solutions for transporting additional medical equipment alongside IV stands are often haphazard and create undue risk of accidents. The risk is compounded when the additional medical equipment is heavy, bulky, fragile, and/or includes multiple lengths of tubing and/or electrical lines.

SUMMARY OF THE INVENTION

Some embodiments of the present disclosure relate to an equipment caddy for demountable engagement with a rolling stand. The caddy comprises a hub defining an opening for receiving therethrough a vertically oriented pole of the stand, and a housing defining at least one compartment that is distal to the hub and configured to demountably receive therein a piece of equipment.

In some embodiments, the caddy is a medical equipment caddy for demountably engaging with a rolling IV stand, wherein the housing is configured to demountably engage with a piece of medical equipment. In some embodiments, the compartment comprises a plurality of compartments. In some embodiments, the plurality of compartments are radially disposed about the hub. In some embodiments, each of the plurality of compartments is configured to demountably receive therein a different piece of medical equipment. In some embodiments, the piece of medical equipment may be a pump, a monitor, an oxygen tank, a catheter collection vessel, an emergency location device, the like, and combinations thereof. In some embodiments, the caddy may further comprise a cavity configured to demountably receive therein one or more personal items. In some embodiments, the personal item may be a purse, a wallet, a key, an electronic device, a book, a magazine, a cosmetic item, a visual aid, or a combination thereof. In some embodiments, the hub is integral to the housing. In some embodiments, the housing is made of a ferrous material or a non-ferrous material.

BRIEF DESCRIPTION OF THE DRAWINGS

These and other features of the present disclosure will become more apparent in the following detailed description in which reference is made to the appended drawings. The appended drawings illustrate one or more embodiments of the present disclosure by way of example only and are not to be construed as limiting the scope of the present disclosure.

FIG. 1 shows a conventional IV stand as known from the prior art;

FIG. 2A shows a perspective view of a medical equipment caddy according to an embodiment, while

FIG. 4A is a close-up perspective view of a clamp, according to an embodiment, shown engaged with a conventional IV stand whereby the medical equipment caddy shown in FIG. 3, may be clamped into a desired position along the IV stand, while

FIG. 3 shows, in perspective view, a medical equipment caddy in accord with an embodiment demountably engaging with a conventional IV stand.

DETAILED DESCRIPTION

Figure 2A:
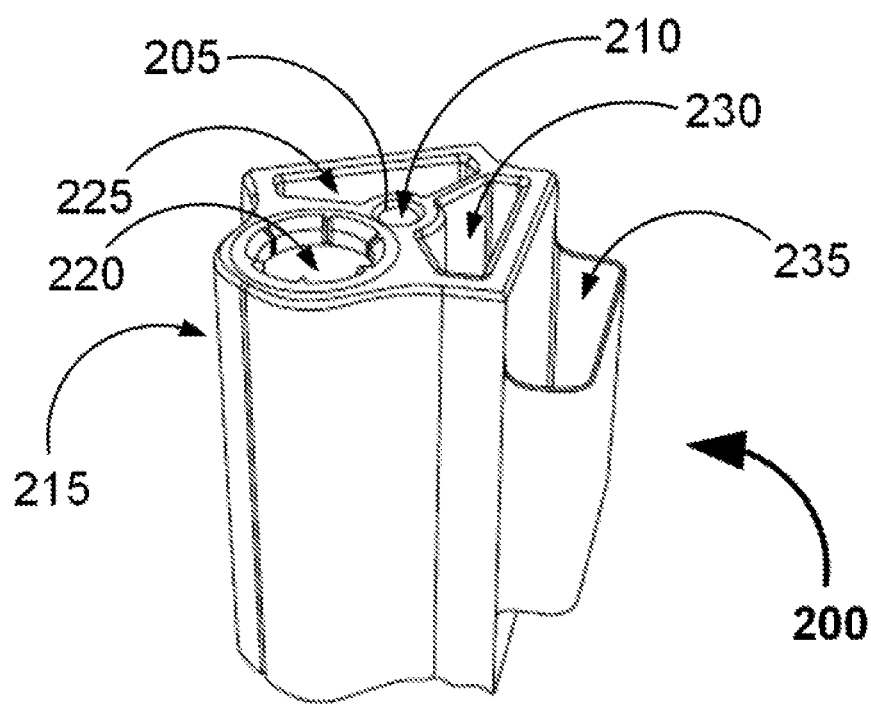

As conventional IV stands do not adequately address the needs of ambulatory IV patients requiring additional medical equipment, there exists an unmet need for a means of transporting additional medical equipment alongside a conventional IV stand in a simple, organized, and intuitive way. The present disclosure contemplates this need and provides a medical equipment caddy that is readily demountably engagable with a conventional IV stand.

FIG. 1 shows an example of a conventional IV stand 100 known in the art. The stand 100 includes a base assembly 105 having a plurality of legs 110, each leg having a castor 115 to enable rolling movement of the stand 100. The stand 100 also includes a support pole 120 which extends vertically upward from the base assembly 105. The stand 100 also includes a hanger assembly 125, which is connected approximate the top of the support pole 120. The hanger assembly has a hanger arm 130 and a hanger 135.

Some embodiments of the present disclosure will now be described by reference to FIGS. 2A and 2B which shows an example of a medical equipment caddy according to the present disclosure.

Figure 2B:
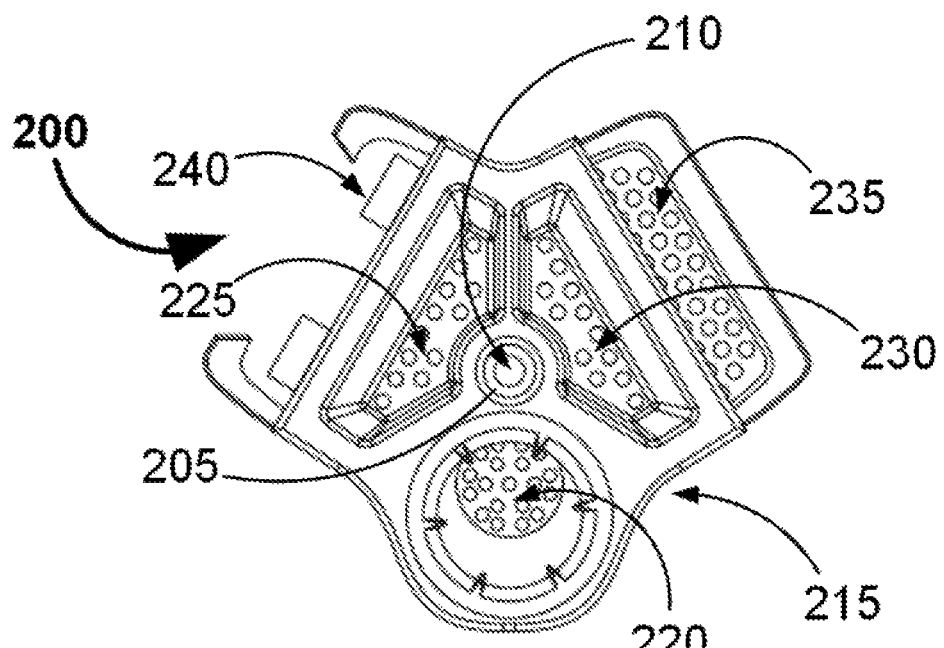
FIG. 2B shows a plan view of the medical equipment caddy.

FIGS. 2A and 2B show an example of a medical equipment caddy 200 in perspective and plan views (FIGS. 2A, and 2B, respectively). The caddy 200 is configured for demountably engagement with a rolling IV stand (for example the stand 100 in FIG. 1). The caddy 200 comprises a hub 205 and a housing 215. The hub 205 defines an opening 210 for receiving therethrough the vertically oriented pole 120 of the rolling IV stand 100. The housing 215 defines a plurality of compartments 220, 225, 230, 235, and 240 that are distal to the hub 205. The compartments 220, 225, 230, 235, and 240 are configured to demountably receive therein various pieces of medical equipment. For example, the compartment 220 may be dimensioned to demountably receive a cylindrical piece of medical equipment such as an oxygen tank. As a further example, the compartment 235 may be dimensioned to demountably receive therein, and occlude the view of, a piece of medical equipment which a patient and/or their healthcare professional wishes to transport discreetly such as a catheter collection vessel. As a further example, the compartment 240 may be dimensioned to demountably receive therein, without occluding the view of, a piece of medical equipment which a patient and/or their healthcare professional wishes to keep accessible such as a PLEUR-EVAC®chest drainage system (PLEUR-EVAC is a registered trademark of Teleflex Medical Inc., Wayne, Pa., USA). As a further example, the compartments 225 and 230 may be dimensioned to demountably receive therein at least one peripheral component of the medical equipment demountably engaged with one or more of the compartments 220, 235, 240 (such as a line, a cord, a monitor, or combinations thereof). The compartments 225 and 230 may also be dimensioned to demountably receive therein an additional piece of medical equipment (such as an infusion pump), or a patient personal item (such as a purse). One or more of the compartments 220, 225, 230, 235, and 240 may be dimensioned to demountably receive a piece of medical equipment or a patient personal item in a protective manner.

Figure 3:
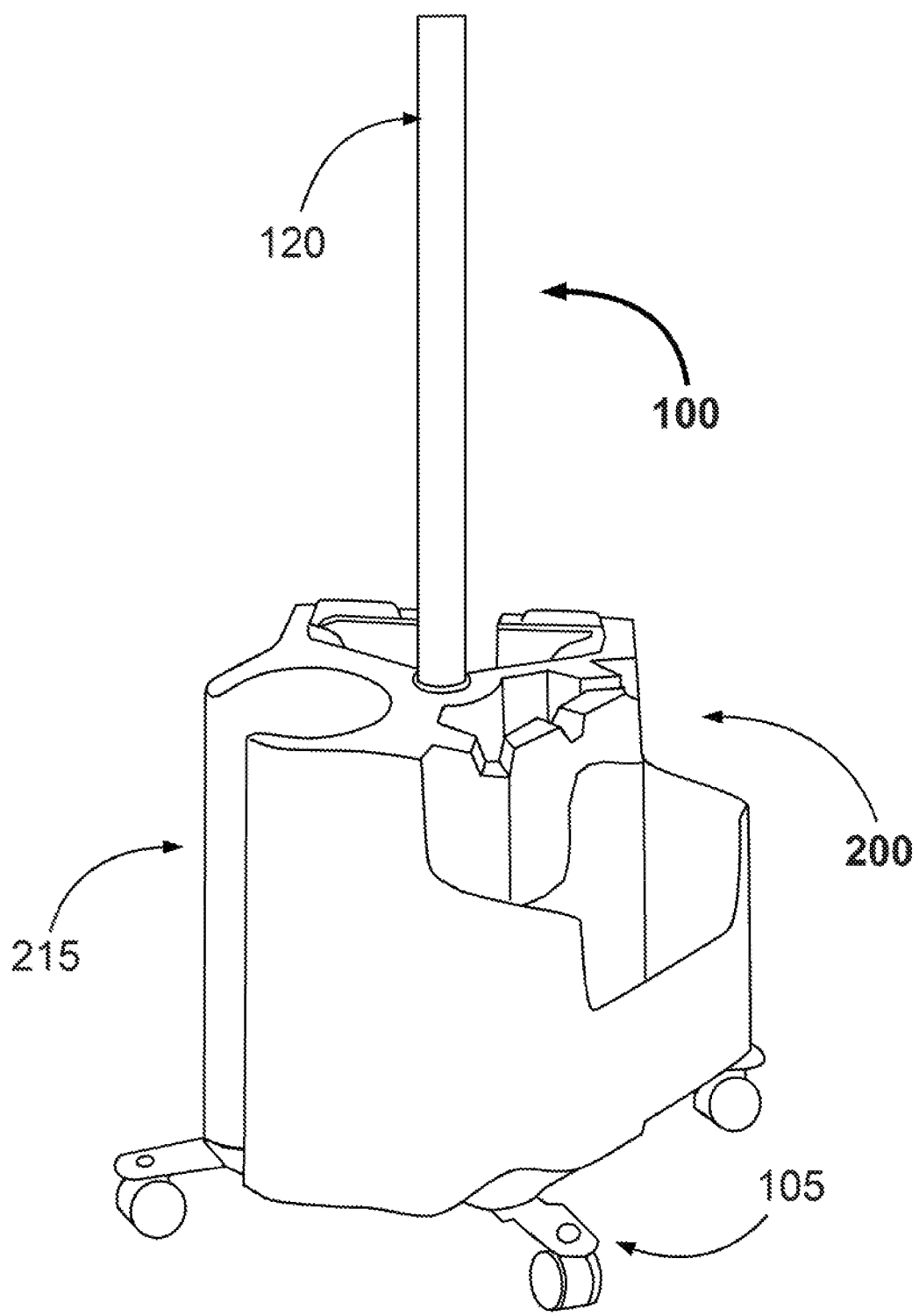
FIG. 3 shows, in a perspective view, a medical equipment caddy in accord with an embodiment demountably engaging with a conventional IV stand.
Figure 4A:
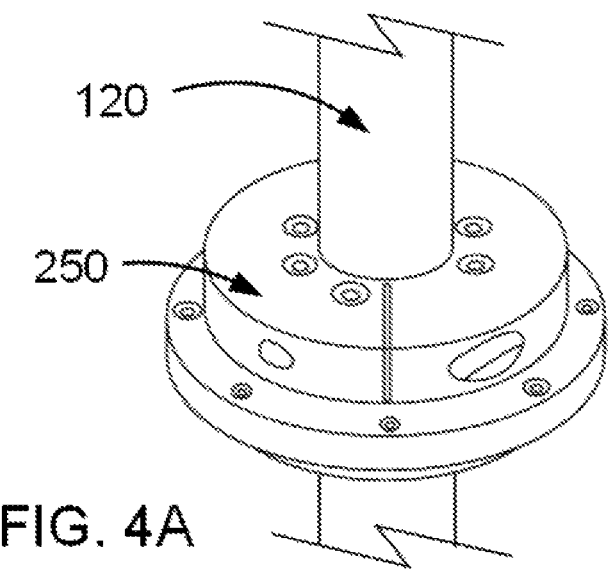
Figure 4B:
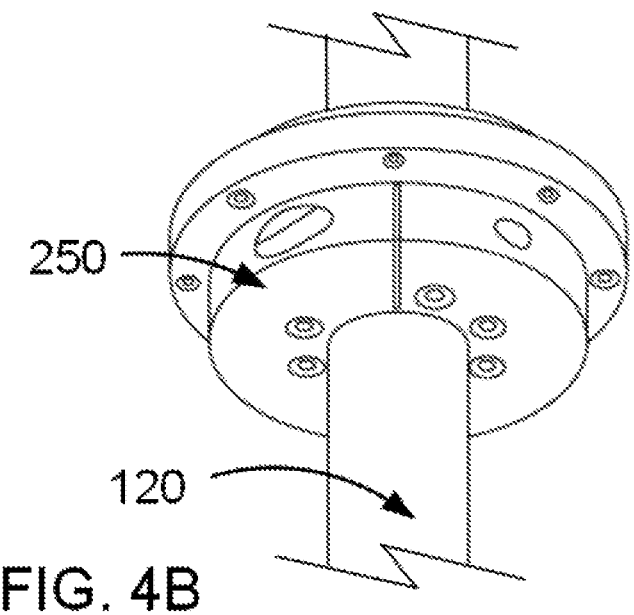
FIG. 4B is another close-up perspective view of the clamp shown engaged with a conventional IV stand whereby the medical equipment caddy my be supported by the claim at a desired location along the IV stand.

FIG. 3 shows an alternate embodiment of the medical equipment caddy 200 demountably engaged with the conventional IV stand 100. In this embodiment, the housing 215 rests on the base assembly 105 and encloses the support pole 120.

It is within the scope of this disclosure to vary the features of the caddy 200. The caddies 200 shown in FIGS. 2A, 2B, and 3 represent only two of many embodiments that fall within the scope of the appended claims. Likewise many of the features of the stand 100 may be varied, and the stand 100 shown in FIG. 1, is only one of many embodiments to which the caddy 200 may be demountably engaged. A non-limiting set of variations and alternate embodiments of the stand 100 and the caddy 200 will now be described.

The caddy 200 may be demountably engaged with various embodiments of the stand 100. For example, the base assembly 105 may be varied at least as follows. The number of legs in the plurality of legs 110 may be from 3 to 6. The number of castors 115 may be from 0 to 12. The length of the legs in the plurality of legs 110 may be from 1.8 m to 1.2 m. The shape of the legs in the plurality of legs 110 may be substantially straight or arced. The radius of the castors 115 may be from 0.5 cm to 25 cm. The castors 115 may be unidirectional castors or swivel castors. And, the castors 115 may be lockable castors or free-rolling castors.

As a further example, the support pole 120 may be varied at least as follows. The support pole 120 may be integral or non-integral to the base assembly 105. The support pole 120 may be sectionable or non-sectionable. The support pole 120 may be telescopic or non-telescopic. The length of the support pole 120 may be from 0.3 m to 3 m; the width of the support pole 120 may be from 3 mm to 10 cm; and the cross-sectional shape of the support pole 120 may be circular, square, rectangular, elliptical, tear-drop, asymmetrical, or the like.

As a further example, the hanger assembly 125 may be varied at least as follows. The hanger arm 130 may be a single hanger arm 130 or a plurality of from 1 to 6 hanger arms 130. The hanger 135 may be a single hanger 135 or a plurality of from 0 to 48 hangers 135. The number of hangers 135 per hanger arm 130 may be from 0 to 10. The length of the hanger arms 130 may be from 3 cm to 1.2 m; the width of the hanger arms 130 may be from 3 mm to 20 cm. The cross-sectional shape of the hanger arms 130 may be may be circular, square, rectangular, elliptical, tear-drop, asymmetrical, or the like.

As a further example, the stand 100 may be equipped with one or more IV stand accessories. IV stand accessories may include, but are not limited to, handles, clamps, and trays.

As a further example, the stand 100 may be configured for use with a wheel chair. In this example, it should be noted that the term "ambulatory patient" refers to a patient who is capable of moving by walking or, alternatively, rolling in a wheelchair.

As noted above, features of the caddy 200 may be varied in numerous ways. For example, the hub 205 may be varied at least as follows. The hub 205 may be integral or non-integral to the housing 215. For example, the hub 205 may be non-integral in that it may be a mass-produced component that is fixed to the housing 215 with a fastener such as an adhesive. Preferably the hub 205 is integral to the housing 215. The hub 205 may be made of a ferrous material or a non-ferrous material. For example, the hub 205 may be made of an alloy (such as an aluminum alloy), a plastic, a metal, or combinations thereof. In a preferred embodiment, the hub 205 is made of plastic such as injection-molded plastic, pour-molded plastic, or blow-molded plastic. The opening 210 defined by the hub 205 may be generally circular, oval-shaped, square-shaped, teardrop-shaped, rectangular, or asymmetrical. In a preferred embodiment, the opening 210 is circular. The width of the opening may be from 3 mm to 10 cm.

As a further example, the housing 215 may be varied at least as follows. The housing 215 may be made of a ferrous material or a non-ferrous material. For example, the housing 115 may be made of an alloy (such as an aluminum alloy), a plastic, a metal, or combinations thereof. In a preferred embodiment, the housing 215 is made of plastic such as injection-molded plastic, pour-molded plastic, or blow molded plastic. The number of the compartments defined by the housing 215 may be from 1 to 20. In embodiments where the number of compartments is greater than one, the compartments may be radially disposed about the hub 205. In embodiments where the number of compartments is greater than one, the compartments may be concentrically disposed about the hub 205. In embodiments where the number of compartments is greater than one each of the compartments may be configured for demountable engagement with a different piece of medical equipment for example, a pump, a monitor, an oxygen tank, a catheter receiving vessel, an emergency location device, the like, and combinations thereof.

As a further example, the housing 215 may define a cavity configured to demountably engage with a personal item. A personal item may include, but is not limited to, a purse, a wallet, a key, an electronic device, a book, a magazine, a cosmetic item, a visual aid, or combinations thereof.

As a further example, the caddy 200 may demountably engage with the IV stand 100 in a variety of different ways.

For example, the caddy 200 may engage the support pole 100 at any point along its length. For example, the caddy 200 may engage the support pole 120 at or near the base assembly 105, at or near the hanger assembly 125, or any point therebetween. The means by which the caddy 200 engages the stand 100 may also vary. For example, the hub 205 may include a fastener such as a screw, a nail, a pin, a hook, or the like for fastening to the support pole 120. Moreover, the hub 205 may comprise a hinge or a clamp 250 configured to demountably engage the support pole 120. Likewise, the caddy 200 may further comprise an adapter member which may be positioned between the housing 215 and the base assembly 105 of the stand 100. The adapter member may have a first surface configured to engage the plurality legs 110 and a second surface configured to engage the housing 215. The adapter member may engage both the plurality of legs 110 and the housing 215 in a rotationally-fixed manor such that the caddy 200 does not rotate relative to the base assembly 105. The adapter member may be integral or non-integral to the housing 215.

In some embodiments, the caddy 200 may comprise a demountable battery module. The battery module may comprise a receptacle configured to demountably engage a battery pack for powering the medical equipment that may demountably engaged with at least one of the compartments of the housing 215. The battery module may comprise a single-prong plug or socket, a two-prong plug or socket, or a three-prong plug or socket. The battery module may also be used to power electronic components that are configured to collect, transmit, and/or analyze data. In some embodiments, the caddy 200 may include a power bar for receiving electrical plugs from the medical equipment that is demountably engaged with the compartments of the housing 215.

In some embodiments, the caddy 200 may be configured for ease of cleaning and/or disinfecting. For example, the caddy 200 may be made of a material that is pressure-washable, machine-washable, chemical resistant, sterilisable, anti-bacterial, or combinations thereof. Optionally, the compartments of the housing 215 may be perforated to facilitate fluid drainage and to improve drying speed.

In addition to the medical equipment caddy embodiments discussed above, the caddy of the present disclosure may be used in other applications. For example, the caddy may be used in assembling, maintaining, or repairing a land-based vehicle, an air-based vehicle, or a water-based vehicle. The caddy may also be used in assembling, maintaining, or repairing a facility or an appliance. The caddy may also be used in a physiotherapy practice, a dental practice, or a chiropractic practice. This wide variety of applications results, at least in part, from the modularity of the caddy which may be easily configured to fit a variety of items.

In the present disclosure, all terms referred to in the singular form are meant to encompass plural forms of the same. Likewise, all terms referred to in plural form are meant to encompass singular forms of the same.

The invention claimed is:

1. An equipment caddy for demountable engagement with a rolling stand, said rolling stand having a base assembly formed by a plurality of identical legs having proximal ends and distal ends, said plurality of legs interconnected at their proximal ends and having castors mounted to their distal ends, and a vertically oriented pole engaged with and extending upward from the interconnected proximal ends of the plurality of legs, the caddy consisting of:
   a hub defining an opening for receiving therethrough the vertically oriented pole of the rolling stand, said hub comprising a fastener for demountably engaging the caddy with the rolling stand; and
   a housing defining a plurality of compartments radially disposed about the hub, wherein
   a first compartment is dimensioned to receive and house therein an oxygen tank, said first compartment having a depth of about 18 inches and a diameter of about 5 inches,
   a second compartment is dimensioned to receive and house therein a catheter collection vessel, said second compartment having a depth of about 18 inches and a diameter of about 5 inches,
   a third compartment is dimensioned to receive and house therein a chest drainage system, said third compartment having a depth of about 12 inches, a length of about 11 inches, and a width of about 4 inches,
   a fourth compartment is dimensioned to receive and house therein an infusion pump, said fourth compartment having a depth of about 12 inches, a length of about 11 inches, and a width of about 4 inches,
   a fifth compartment is dimensioned as a shallow tray, said fifth compartment having a depth of about 1 inch, a length of about 8 inches, and a width of about 4 inches;
   and wherein the housing is configured to rest on the plurality of legs of the rolling stand.

2. The caddy of claim 1, wherein the hub is integral to the housing.

3. The caddy of claim 1, wherein the hub further comprises a clamp for demountably clamping the caddy to the vertically oriented pole of the rolling stand.

* * * * *